United States Patent [19]

Uggeri et al.

[11] Patent Number: 5,663,413
[45] Date of Patent: Sep. 2, 1997

[54] BIPHENYL IODINATED DERIVATIVES AND THEIR DIAGNOSTIC USE

[75] Inventors: Fulvio Uggeri; Pier Lucio Anelli; Marino Brocchetta; Massimo Visigalli, all of Milan, Italy

[73] Assignee: Dibra S.p.A., Milan, Italy

[21] Appl. No.: 448,750

[22] Filed: May 24, 1995

[30] Foreign Application Priority Data

Dec. 1, 1994 [IT] Italy .................................. MI94A2433

[51] Int. Cl.⁶ .......................... C07C 69/76; C07C 233/11; C07C 17/00
[52] U.S. Cl. .......................... 560/59; 564/156; 564/158; 564/180; 564/209; 562/451; 562/469; 570/203; 570/204; 570/206
[58] Field of Search ........................ 560/42, 59; 562/451, 562/469; 564/156, 158, 180, 209; 570/203, 204, 206

[56] References Cited

U.S. PATENT DOCUMENTS

| 4,792,642 | 12/1988 | Rule et al. | 570/203 |
| 5,043,152 | 8/1991 | Schaefer | 564/153 |
| 5,066,823 | 11/1991 | Felder et al. | 560/13 |
| 5,370,861 | 12/1994 | Klaveness et al. | 558/275 |
| 5,463,080 | 10/1995 | Ogan et al. | 560/47 |
| 5,464,607 | 11/1995 | Anelli et al. | 564/153 |

FOREIGN PATENT DOCUMENTS

| WO92/14695 | 9/1992 | WIPO . | |
| WO95/01966 | 1/1995 | WIPO | 564/156 |

*Primary Examiner*—Mark D. Sweet
*Attorney, Agent, or Firm*—Bucknam and Archer

[57] ABSTRACT

The invention relates to novel contrast media particularly useful for X-ray diagnostic investigations of human and animal body.

6 Claims, No Drawings

BIPHENYL IODINATED DERIVATIVES AND THEIR DIAGNOSTIC USE

This invention relates to novel contrast media particularly useful for X-ray diagnostic investigations of human and animal body and comprises novel compounds of general formula (I):

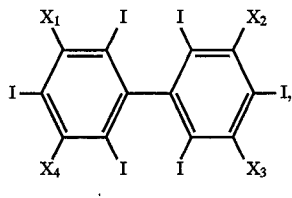

wherein:
$X_1$, $X_2$, $X_3$, $X_4$ independently are H or a —O—B group or a —Y—Z group, with the proviso that at least one of said $X_{1\rightarrow 4}$ substituents is H or a —O—B group, and wherein B is H or ($C_1$-$C_6$) hydroxyalkyl residue, with 1-5 —OH groups or a polyoxaalkyl group of formula

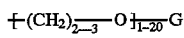

wherein
G is H, —$CH_3$ or —$CH_2$—$CH_3$, or
B is one of the groups of formula

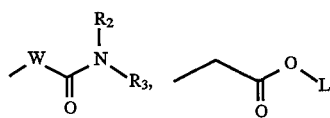

wherein
W is a —$(CH_2)_{0-5}$—$CH(R_1)$— group,
$R_1$ is H or a $CH_3$ group,
$R_2$ and $R_3$, which can be the same or different, are H or a ($C_1$-$C_6$) alkyl group or a ($C_1$-$C_6$) hydroxyalkyl residue with 1-5 —OH groups, or a ($C_2$-$C_6$) alkoxyalkyl residue, or they are a polyoxaalkyl group as previously defined, or $R_2$ and $R_3$, taken together, form a ($C_3$-$C_6$) chain, which can be substituted or not by —O—, —X—, —NH—, —N($CH_3$)— groups, and
L is H or a ($C_1$-$C_6$) alkyl residue, or a ($C_1$-$C_6$) hydroxyalkyl residue, with 1-5 —OH groups;
Y is a —CO— group or a —N(D)— group, wherein
a) when Y is equal to —CO—, then Z is a —$NR_2R_3$ group wherein $R_2$ and $R_3$ are as previously defined and
b) when Y is equal to —N(D)—, then D is H or a ($C_1$-$C_6$) alkyl residue, or a ($C_1$-$C_6$) hydroxyalkyl residue, with 1-5 —OH groups, and Z is a —$COR_4$ group, wherein $R_4$ is a ($C_1$-$C_6$) hydroxyalkyl residue with 1-5 —OH groups,
with the proviso that all the $X_{1-4}$ substituents are not simoultaneously H or —O—B.

When the compounds of formula (I) contain one or more phenol functions, this invention comprise also the salts of said compounds with physiologically acceptable organic bases selected from primary, secondary and tertiary amines, or basic amino acids or inorganic bases whose cations are sodium, potassium, magnesium, calcium, or mixtures thereof.

Current X-ray contrast media preferably contain, as opacifying molecules, polyiodinated neutral aromatic compounds (see for instance D. P. Swanson et al "Pharmaceuticals in Medical Imaging", 1990, Mac Millan Publ. Company).

These products contain at least a benzene nucleus in which three hydrogen atoms are substituted with three iodine atoms. A good X-ray absorption requires a high iodine concentration and consequently said contrast agents are used in highly concentrated solutions, which can cause undesirable side effects (pain, high temperature, nausea, low pressure and vasal damages) due to hypertonicity and a viscosity higher than blood.

The products of the present invention are novel iodinated biphenyl derivatives characterized by the presence of 6 iodine atoms on the aromatic nuclei.

The derivatives of this invention have never been disclosed nor previously suggested. For instance, patent application EP-A-501875 (Guerbet) claims the following general formula:

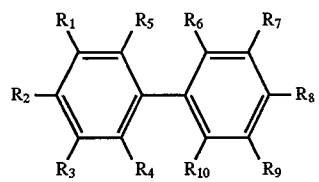

wherein $R_1$-$R_{10}$ can be a iodine atom or a group having the following formulae:

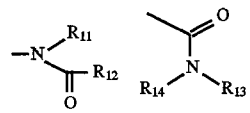

However, said derivatives do not absolutely comprise compounds in which there are one or more oxygenated functions directly bound to aromatic rings, nor comprise the cases in which $R_1$-$R_{10}$ are hydrogen atoms, as well as they do not claim nor indicate other compounds of this invention.

Preferred compounds of this invention are those of general formula (II),

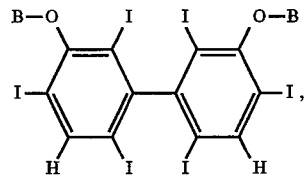

wherein one of $X_{1\rightarrow 4}$ groups is hydrogen and the remaining ones are a —O—B residue as defined above.

Other preferred compounds are those of general formula (III),

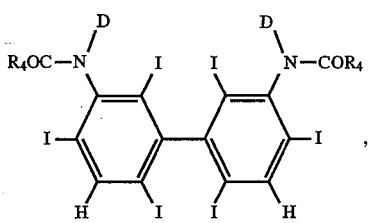

wherein two of $X_{1\rightarrow 4}$ groups is hydrogen and the remaining ones are a —N(D)$COR_4$ residue as defined above.

Equally preferred are the compounds of general formula (IV),

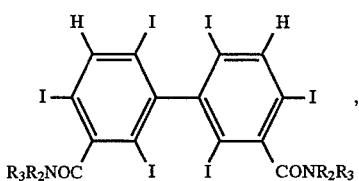

(IV)

wherein two of $X_{1\rightarrow 4}$ groups is hydrogen and the remaining ones are a —$CONR_2R_3$ group as defined above.

Particularly preferred are the compounds of general formula (V),

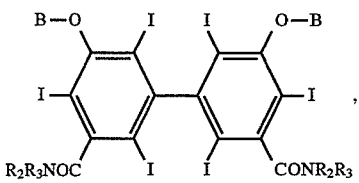

(V)

wherein —O—B and —$CONR_2R_3$ substituents are as defined above.

The compounds of this invention can be prepared according to known and commonly used synthetic ways for the preparation of iodinated contrast agents.

In particular the compounds of general formula (III) can be easily prepared by Smiles rearrangement, according to the procedure disclosed in patent EP 365541 (Bracco), from products of general formula (II), in the specific case in which B is a —$CH_2$—$CONHR_3$ group, wherein $R_3$ is the residue D as defined above.

The products of this invention are generally characterized by a high solubility, low viscosity and osmolality, as well as high intravenous, intracisternal and intracerebral tolerability.

The compounds of this invention, in view of their diagnostic use, can be bound to or encapsulated into biomolecules or macromolecules which are aimed at selectively concentrate in the organ or the tissue under examination. Organ selectivity can be achieved, for instance, thanks to the encapsulation of said compounds into liposomes.

The compounds of this invention have a wide range of applications, since they can be used for intravasal, (for instance intravenous, intraarterial, intracoronaric, intraventricular administration and so on), intrathecal, intraperitoneal, intralymphatic, intracavital and intraparenchymal administrations. Both soluble and less soluble compounds are suitable for oral or enteral administration, and therefore, specifically for the gastrointestinal tract imaging (GI). For the parenteral administration they can preferentially be formulated as sterile aqueous solutions or suspensions, whose pH can range from 6.0 to 8.5, optionally using physiologically acceptable basic buffering agents (for example tris[hydroxymethyl]aminomethane or TRIS).

These formulations can also be lyophilized and reconstituted for their use. For GI use or for injection into body cavities, these agents can be formulated as a solution or suspension containing suitable additives, for example, to control viscosity.

For the oral administration they can be formulated according to preparation methods routinely used in the pharmaceutical technique: excipients, such as sweeteners or flavouring agents, can also be added according to known pharmaceutical formulation techniques.

As various changes could be made in the above compositions and methods without departing from the scope of the invention, it is intended that all matter contained in the above description shall be interpreted as illustrative and not in a limiting sense.

EXAMPLE 1

3,3'-Bis(3,6,9,12,15,18,21-heptaoxadocos-1-yloxy)-2,2',4,4',6,6'-hexaiodo-1,1'-biphenyl

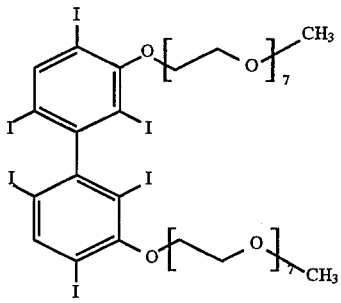

A) 2,2',4,4',6,6'-Hexaiodo-1,1'-biphenyl-3,3'-diol

A solution of 15.08 g (81 mmol) of 1,1'-biphenyl-3,3'-diol (CAS RN 612-76-0) in 830 mL of a $H_2O$: $CH_3CN$=1:1 mixture, at room temperature, is added with 220 g (780 mmol) of a ICl solution (45% I; 16% HCl) in HCl. After 6 h at room temperature, the suspension is heated to 35°–40° C. and MeOH (550 mL) is added to obtain a solution. After 100 h the solution is treated with $Na_2S_2O_3$, concentrated under vacuum and diluted with $H_2O$ (340 mL), to precipitate a solid which is filtered, washed and dried. The crude is purified by crystallization from acetone to give 62.54 g (66 mmol) of the desired product.

Yield: 81%

$^1$H-NMR, $^{13}$C-NMR, IR and MS spectra are consistent with the structure.

B) 4-nitrobenzenesulfonic acid 3,6,9,12,15,18,21-heptaoxadocos-1-yl ester 6.7 g (60 mmol) of TEA are dropwise added, in 10 min, to a solution of 13.3 g (60 mmol) of 4-nitrobenzenesulfonyl chloride (marketed product) and of 20.4 g (60 mmol) of 3,6,9,12,15,18,21-heptaoxadocosan-1-ol (according to Liebigs Ann. Chem. 1980, 858–862) in 60 mL of AcOEt. After 2 h at the temperature of 20° C., the precipitated TEA hydrochloride is filtered off, washing with 10 mL of AcOEt for three times. The filtrates are collected, washed with 30 mL of $H_2O$, 20 mL of 2N HCl and then with $H_2O$ to reach a neutral pH. The organic phase is evaporated to dryness, to give a thick oil which is directly used in the successive step without a further purification. 25 g (47 mmol) of the desired product are obtained.

Yield: 79%

$^1$H-NMR, $^{13}$C-NMR, IR and MS spectra are consistent with the structure.

C) Title compound

A solution of 15.06 g (16 mmol) of compound A) in 320 mL of DMA is added with 16 mL (32 mmol) of 2N MeONa in MeOH and, after evaporation of MeOH, with 25.23 g (48 mmol) of compound B). The reaction mixture is heated at 70° C. for 6 h. The solution is evaporated under vacuum and the resulting oily residue is treated with $CH_2Cl_2$. The resulting solid is discarded whereas the solution is washed with $H_2O$, dried and concentrated to dryness. The residue is treated with AcOEt to give 17.45 g (11 mmol) of the desired product.

Yield: 69%

$^1$H-NMR, $^{13}$C-NMR, IR and MS spectra are consistent with the structure.

EXAMPLE 2

1,1'-[(2,2',4,4',6,6'-Hexaiodo-1,1'-biphenyl)-3,3'-diylbis[oxy(1-oxo-2,1-ethanediyl)methylimino]]bis[1-deoxy-D-glucitol]

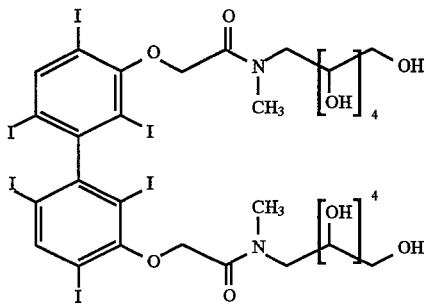

A) 2,2'-[(2,2',4,4',6,6'-hexaiodo-1,1-biphenyl)-3,3'-diylbis-(oxy)]bisacetic acid dimethyl ester A solution of 51.79 g (55 mmol) of 2,2',4,4',6,6'-hexaiodo-1,1'-biphenyl-3,3'-diol (prepared according to EXAMPLE 1) in 1.1 l of DMA is added with 55 mL (110 mmol) of 2N MeONa in MeOH; after evaporation of MeOH, 29.17 g (187 mol) of BrCH$_2$COO$_2$MeO are added heating at 60° C. for 3 h. The solvent is evaporated off to obtain a residue which is dissolved in CH$_2$Cl$_2$, and the solution is washed with H$_2$O, dried with Na$_2$SO$_4$ and concentrated to dryness. 45.6 g (42 mmol) of the desired product are obtained.

Yield: 76%

$^1$H-NMR, $^{13}$C-NMR, IR and MS spectra are consistent with the structure.

B) Title compound

A solution of 9.6 g (8.84 mmol) of compound A) in 130 mL of MeOH heated at 50° C. is added with 11.22 g (57.46 mmol) of N-methylglucamine, heating at 50° C. for about 5 h. The reaction mixture is reduced to one third of the volume and cooled at room temperature. The crystallized solid is filtered, washed and dried; the crude is purified by crystallization from MeOH to give 7.73 g (5.57 mmol) of the desired product.

Yield: 63%

$^1$H-NMR, $^{13}$C-NMR, IR and MS spectra are consistent with the structure.

EXAMPLE 3

2,2'-[(2,2',4,4',6,6'-Hexaiodo-1,1'-biphenyl)-3,3'-diylbis(oxy)]bis[N-(2,3-dihydroxypropyl)acetamide]

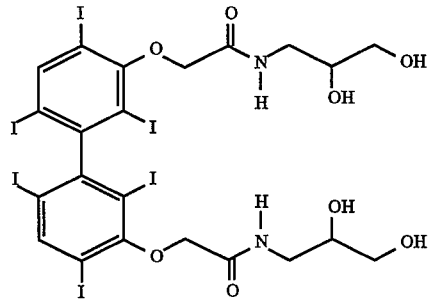

Following the procedure of EXAMPLE 2, 8.7 g (8 mmol) of 2,2'-[(2,2',4,4',6,6'-hexaiodo-1,1-biphenyl)-3,3'-diylbis-(oxy)]bisacetic acid dimethyl ester are reacted with 4.74 g (52 mmol) of isoserinol in 120 mL of MeOH, and refluxed for 20 h. 6.5 g (5.4 mmol) of the desired product are obtained.

Yield: 68%

$^1$H-NMR, $^{13}$C-NMR, IR and MS spectra are consistent with the structure.

EXAMPLE 4

2,2'-[(2,2',4,4',6,6'-Hexaiodo-1,1'-biphenyl)-3,3'-diylbis(oxy)]bis[N-methylacetamide]

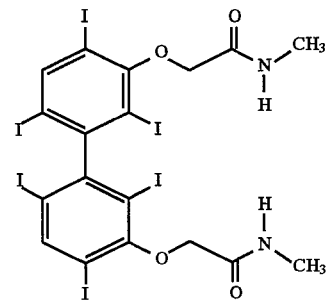

Following the procedure of EXAMPLE 2, 10.75 g (9.9 mmol) of 2,2'-[(2,2',4,4',6,6'-hexaiodo-1,1-biphenyl)-3,3'-diylbis-(oxy)]bisacetic acid dimethyl ester are reacted with 5 g (64.4 mmol) of 40% aq. MeNH$_2$ in 150 mL of MeOH. 8.78 g (8.1 mmol) of the desired product are obtained.

Yield: 82%

$^1$H-NMR, $^{13}$C-NMR, IR and MS spectra are consistent with the structure.

EXAMPLE 5

3,3'-[(2,2',4,4',6,6'-Hexaiodo-1,1'-biphenyl)-3,3'-diylbis[(2-hydroxy-1-oxoethyl)imino]bis[1,2-propanediol]

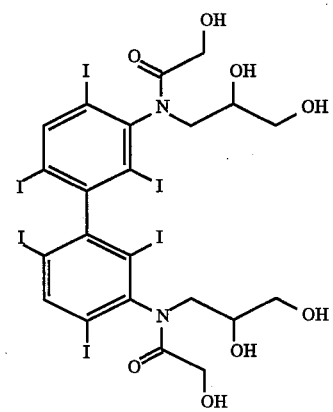

A suspension of 6.02 g (5 mmol) of 2,2'-[(2,2',4,4',6,6'-hexaiodo-1,1'-biphenyl)- 3,3'-diylbis(oxy)]bis[N-(2,3-dihydroxypropyl)-acetamide] (prepared according to EXAMPLE 3) in 25 mL of H$_2$O is added with 0.05N NaOH up to pH 9, and the reaction mixture is kept at 90° C. for 5 h. The solution is then neutralized, concentrated to half the volume, cooled and filtered. The aqueous solution is then percolated through a cation exchange resin Duolite® C 20 MB and then on an anion exchange resin Duolite® A 30 B, eluting with water; the neutral eluate is evaporated and the residue is crystallized from EtOH to give 4.94 g (4.1 mmol) of the desired product.

Yield: 82%

$^1$H-NMR, $^{13}$C-NMR, IR and MS spectra are consistent with the structure.

EXAMPLE 6

N,N'-[(2,2',4,4',6,6'-Hexaiodo-1,1'-biphenyl)-3,3'-diyl]bis[(N,N'-dimethyl)-2-hydroxyacetamide]

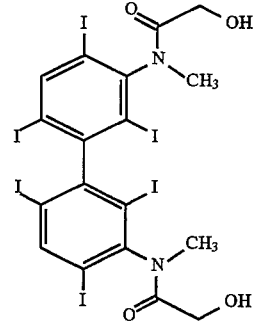

A suspension of 8.13 g (7.5 mmol) of 2,2'-[(2,2',4,4',6,6'-hexaiodo-1,1'-biphenyl)-3,3'-diylbis(oxy)]bis[N-methylacetamide] (prepared according to EXAMPLE 4) in 40 mL of H$_2$O and 3.75 mL (0.375 mmol) of 0.1N NaOH is heated at 90° C. for about 1 h to obtain a gradual dissolution. After cooling at room temperature, the solution is percolated through a cation exchange resin Duolite® C 20 MB and then through an anion exchange resin Duolite® A 30 B, eluting with water; the neutral eluate is concentrated to dryness and the residue is crystallized from EtOH to give 5.85 g (5.4 mmol) of the desired product.

Yield: 72%

$^1$H-NMR, $^{13}$C-NMR, IR and MS spectra are consistent with the structure.

EXAMPLE 7

2,2'-[(2,2',4,4',6,6'-hexaiodo-1,1'-byphenyl)-3,3'diylbis(oxy)]-bisacetic acid

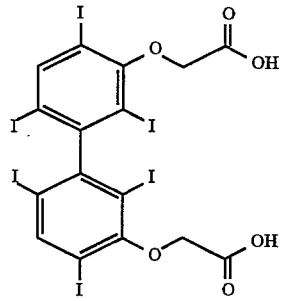

A suspension of 10.86 g (10 mmol) of 2,2'-[(2,2',4,4',6,6'-hexaiodo-1,1'-biphenyl)-3,3'-diylbis(oxy)]bisacetic acid dimethyl ester (prepared according to EXAMPLE 2) in 150 mL of H$_2$O is added with 30 mL (30 mmol) of 1N NaOH at room temperature to obtain a gradual dissolution; after 2 h the solution is filtered and acidified to pH 1.5 with 37% HCl, to precipitate 10.15 g (9.6 mol) of the desired product.

Yield: 96%

$^1$H-NMR, $^{13}$C-NMR, IR and MS spectra are consistent with the structure.

EXAMPLE 8

N,N'-Bis[2-hydroxy-1-(hydroxymethyl)ethyl]-5,5'-dihydroxy-2,2',4,4',-6,6'-hexaiodo-1,1'-biphenyl-3,3'-dicarboxamide

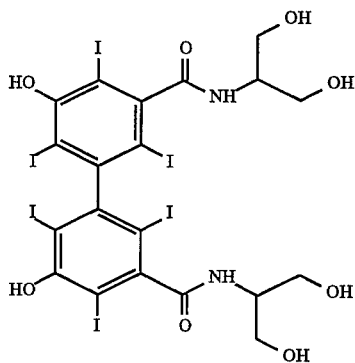

A) 5,5'-diamino-1,1'-biphenyl-3,3'-dicarboxylic acid dimethyl ester

A solution of 30 g (83.3 mmol) of 5,5'-dinitro-1,1'-biphenyl-3,3'-dicarboxylic acid dimethyl ester (prepared according to patent application WO 9404488) in 1.6 L of MeOH is hydrogenated in an autoclave at 60° C. in the presence of 42 g of 10% Pd/C, under a pressure of 6 atm of H$_2$; after 6 h the catalyst is filtered off and the solution is evaporated to dryness to give 23.5 g (78.3 mmol) of the desired product.

Yield: 94%

$^1$H-NMR, $^{13}$C-NMR, IR and MS spectra are consistent with the structure.

B) 5,5'-dihydroxy-1,1'-biphenyl-3,3'-dicarboxylic acid dimethyl ester 20 g (66.6 mmol) of compound A) are suspended in 130 mL of H$_2$O and dissolved by addition of 157 g (400 mmol) of 25% H$_2$SO$_4$. This solution, cooled at 0°–5° C., is added with a solution of 11.04 g (160 mmol) of NaNO$_2$ in 35 mL of H$_2$O in 15 min. After 15 min at 5° C., the reaction mixture is dropwise added, in 30 min, to a solution of 47.3 g (333 mmol) of Na$_2$SO$_4$ and 66.6 g (666 mmol) of 98% H$_2$SO$_4$ in 70 mL of H$_2$O and heated at 70° C. After 2 h at this temperature, the resulting precipitate is filtered, washed with H$_2$O and dried. The resulting crude is purified by crystallization from MeOH to give 15.42 g (51 mmol) of the desired product.

Yield: 77%

$^1$H-NMR, $^{13}$C-NMR, IR and MS spectra are consistent with the structure.

C) N,N'-Bis[2-hydroxy-1-(hydroxymethyl)ethyl]-5,5'-dihydroxy-1,1'-biphenyl-3,3'-dicarboxamide A mixture of 10.3 g (34 mmol) of compound B) and 24.78 g (272 mmol) of 2-amino-1,3-propanediol is heated under vacuum (100° C.; 2.6 KPa) for about 3 h up until MeOH evolution ceases. The fused mass is cooled to 50° C. and dissolved in 100 mL of H$_2$O. The solution is percolated through a cation exchange resin Duolite® C 20 MB and then through an anion exchange resin Duolite® A 30 B, eluting with water; the neutral eluate is concentrated to dryness to give a crude which is crystallized from abs. EtOH to give 8.83 g (21 mmol) of the desired product.

Yield: 62%

$^1$H-NMR, $^{13}$C-NMR, IR and MS spectra are consistent with the structure.

D) Title compound

A solution of 8 g (19 mmol) of compound C) in 60 mL of H₂O is added with 32.15 g (114 mmol) of a solution of ICl (45% I; 16% HCl) and 57 mL (285 mmol) of 5N NaOH, at room temperature in about 3 h, keeping pH 8. The resulting solution is treated with NaHSO₃, filtered and acidified to pH 2 with 37% HCl. The precipitated crude is filtered, washed with H₂O, dried and purified by dissolution in H₂O at pH 8 with 2N NaOH and further reprecipitation at pH 2 with 37% HCl. After filtration, washing with H₂O and drying, 17.64 g (15 mmol) of the desired product are obtained.

Yield: 79%

$^1$H-NMR, $^{13}$C-NMR, IR and MS spectra are consistent with the structure.

EXAMPLE 9

N,N'-Bis[2-hydroxy-1-(hydroxymethyl)ethyl]-5,5'-bis(3,6,9,12,15,18,21-heptaoxadocos-1-yloxy)-2,2',4,4',6,6'-hexaiodo-1,1'-biphenyl-3,3'-dicarboxamide

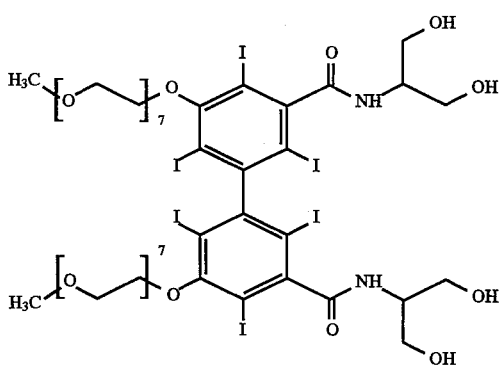

A solution of 8.3 g (6.8 mmol) of N,N'-bis[2-hydroxy-1-(hydroxymethyl)ethyl]-5,5'-dihydroxy-2,2',4,4',6,6'-hexaiodo-1,1'-biphenyl-3,3'-dicarboxamide disodium salt [prepared evaporating to dryness a solution of 8 g (6.8 mmol) of N,N'-bis[2-hydroxy-1-(hydroxymethyl)ethyl]-5,5'-dihydroxy- 2,2',4,4',6,6'-hexaiodo,1,1'-biphenyl-3,3'-dicarboxamide, described in EXAMPLE 8, and 13.6 mL (13.6 mmol) of 1N NaOH in 50 mL of H₂O] in 170 mL of DMA, is added with 11.79 g (22.44 mmol) of 3,6,9,12,15,18,21-heptaoxadocos-1-yl 4-nitrobenzenesulfonate (prepared according to EXAMPLE 1) and the mixture is heated at 70° C. for 7 h. The mixture is then evaporated under vacuum and the oily residue is treated with CH₂Cl₂. The resulting precipitate is filtered and discarded whereas the organic phase is washed with H₂O, dried and evaporated to dryness. The resulting residue is treated with AcOEt at ebullition, cooled to 25° C., filtered and dried, to obtain 8.89 g (4.9 mmol) of the desired product.

Yield: 72%

$^1$H-NMR, $^{13}$C-NMR, IR and MS spectra are consistent with the structure.

EXAMPLE 10

2,2'-[[5,5'-bis[[[2-hydroxy-1-(hydroxymethyl)ethyl]amino]carbonyl]-2,2',4,4',6,6',-hexaiodo-1,1'-biphenyl]-3,3'-diylbis(oxy)]bisacetic acid dimethyl ester

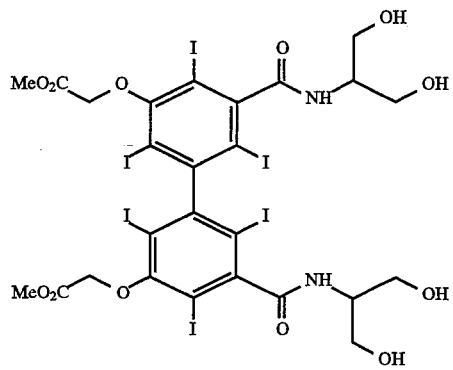

A solution of 9.03 g (7.4 mmol) of N,N'-bis[2-hydroxy-1-(hydroxymethyl)ethyl]-5,5'-dihydroxy-2,2',4,4',6,6'-hexaiodo-1,1'-biphenyl-3,3'-dicarboxamide disodium salt (prepared according to EXAMPLE 9) in 200 mL of DMA, is added with 3.81 g (24.42 mmol) of BrCH₂CO₂Me. Then the solution is heated at 50° C. for 4 h. The solvent is evaporated off under reduced pressure, the oily residue is treated with H₂O, to give a precipitate which is filtered, washed with H₂O and dried. The resulting crude is crystallized from MeOH to give 6.2 g (4.7 mmol) of the desired product.

Yield: 64%

$^1$H-NMR, $^{13}$C-NMR, IR and MS spectra are consistent with the structure.

EXAMPLE 11

N,N'-Bis[2-hydroxy-1-(hydroxymethyl)ethyl]-5,5'-bis[2-[[2-(hydroxyethoxy)ethyl]methylamino]-2-oxoethoxy]-2,2',4,4',6,6'-hexaiodo-1,1'-biphenyl-3,3'-dicarboxamide

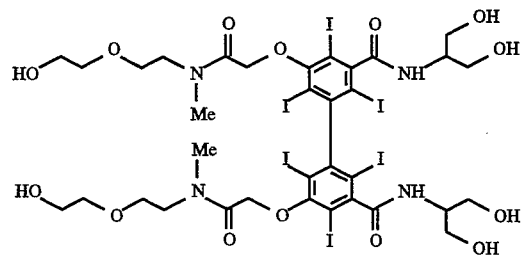

A solution of 5.81 g (4.4 mmol) of 2,2'-[[5,5'-bis[[[2-hydroxy-1-(hydroxymethyl)ethyl]amino]carbonyl]-2,2',4,4',6,6'-hexaiodo-1,1'-biphenyl]-3,3'-diylbis(oxy)]bisacetic acid dimethyl ester (prepared according to EXAMPLE 10) in 70 mL of MeOH, heated at 50° C., is added with 3.4 g (28.6 mmol) of 2-[2-(methylamino)ethoxy]ethanol (CAS RN 85475-01-0). Then the solution is boiled for 4 h; the reaction mixture is evaporated to dryness; the residue is dissolved in H₂O and the solution is percolated through a cation exchange resin Duolite® C 20 MB and then through an anion exchange resin Duolite® A 30 B. The neutral eluate is evaporated to dryness and the residue is crystallized from EtOH to give 5 g (3.4 mmol) of the desired product.

Yield: 77%

¹H-NMR, ¹³C-NMR, IR and MS spectra are consistent with the structure.

EXAMPLE 12

2,2'-[[5,5'-bis[[[2-hydroxy-1-(hydroxymethyl)ethyl]amino]carbonyl]-2,2',4,4',6,6'-hexaiodo-1,1'-biphenyl]-3,3'-diylbis(oxy)]bisacetic acid

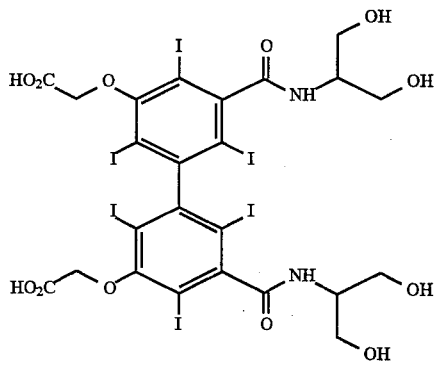

A suspension of 3.96 g (3 mmol) of 2,2'-[[5,5'-bis[[[2-hydroxy-1-(hydroxymethyl)ethyl]amino]carbonyl]-2,2',4,4',6,6'-hexaiodo-1,1'-biphenyl]-3,3'-diylbis(oxy)]bisacetic acid dimethyl ester (prepared according to EXAMPLE 10) in 50 mL of $H_2O$ is added with 7 mL (7 mmol) of NaOH 1N, at room temperature, obtaining a gradual dissolution; after 2 h the solution is filtered and acidified to pH 1.5 with 37% HCl to precipitate 3.62 g (2.8 mmol) of the desired product.

Yield: 93%.

¹H-NMR, ¹³C-NMR, IR and MS spectra are consistent with the structure.

We claim:

1. A compound of general formula (I)

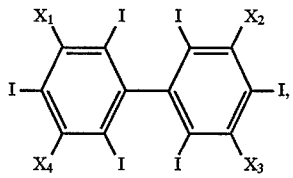

wherein:

$X_1$, $X_2$, $X_3$, $X_4$ independently are H or a —O—B group or a —Y—Z group, with the proviso that at least one of said $X_{1\rightarrow 4}$ substituents is H or a —O—B group, and wherein B is H or ($C_1$-$C_6$) hydroxyalkyl residue, with 1–5 —OH groups or a polyoxaalkyl group of formula

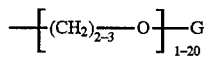

wherein
G is H, —$CH_3$ or —$CH_2$—$CH_3$, or

B is one of the groups of formula

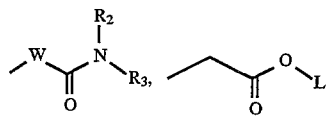

wherein

W is a —$(CH_2)_{0-5}$—$CH(R_1)$— group, $R_1$ is H or a $CH_3$ group, $R_2$ and $R_3$, which can be the same or different, are H or a ($C_1$-$C_6$) alkyl group or a ($C_1$-$C_6$) hydroxyalkyl residue with 1–5 —OH groups, or a ($C_2$-$C_6$) alkoxyalkyl residue, or they are a polyoxaalkyl group as previously defined, or $R_2$ and $R_3$, taken together, form a ($C_3$-$C_6$) chain, which can be substituted or not by —O—, —X—, —NH—, —N($CH_3$)— groups, and L is H or a ($C_1$-$C_6$) alkyl residue, or a ($C_1$-$C_6$) hydroxyalkyl residue, with 1–5 —OH groups;

Y is a —CO— group or a —N(D)— group, wherein
a) when Y is equal to —CO—, then Z is a —$NR_2R_3$ group wherein $R_2$ and $R_3$ are as previously defined and
b) when Y is equal to —N(D)—, then D is H or a ($C_1$-$C_6$) alkyl residue, or a ($C_1$-$C_6$) hydroxyalkyl residue, with 1–5 —OH groups, and Z is a —$COR_4$ group, wherein $R_4$ is a ($C_1$-$C_6$) hydroxyalkyl residue with 1–5 —OH groups, with the proviso that all the $X_{1-4}$ substituents are not simultaneously H or —O—B;

and when said compound of formula (I) contains one or more phenol or free acid functions, these can be salified or not with physiologically acceptable organic bases selected from primary, secondary and tertiary amines, or basic amino acids or inorganic bases whose cations are sodium, potassium, magnesium, calcium, or mixtures thereof.

2. A compound according to claim 1, of general formula (II) and the salts thereof

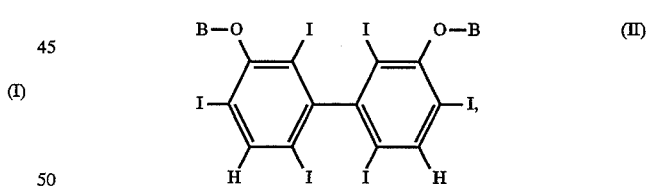

wherein B is as defined in claim 1.

3. A compound according to claim 1, of general formula (III) and the salts thereof

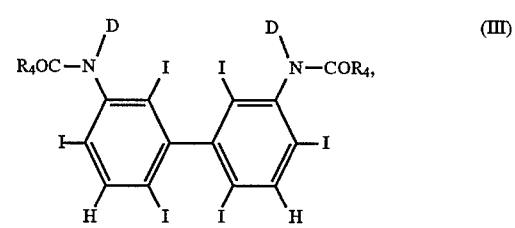

wherein D and $R_4$ are as defined in claim 1.

4. A compound according to claim 1, of general formula (IV) and the salts thereof

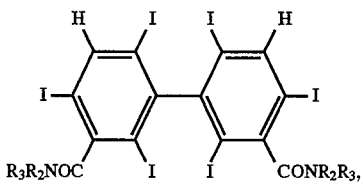

wherein $R_2$ and $R_3$ are as defined in claim 1.

5. A compound according to claim 1, of general formula (V) and the salts thereof

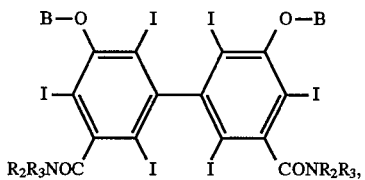

wherein B, $R_2$ and $R_3$ are as defined in claim 1.

6. A compound according to claim 1, selected from the group consisting of:

2,2',4,4',6,6'-hexaiodo-1,1'-biphenyl-3,3'-diol;

3,3'-bis(3,6,9,12,15,18,21-heptaoxadocos-1-yloxy)-2,2', 4,4',6,6'-hexaiodo-1,1'-biphenyl;

2,2'[(2,2',4,4',6,6'-hexaiodo-1,1-biphenyl)-3,3'-diylbis-(oxy)]bisacetic acid dimethyl ester;

1,1'-[(2,2',4,4',6,6'-hexaiodo-1,1'-biphenyl)-3,3'-diylbis [oxy(1-oxo-2,1-ethanediyl)methylimino]]bis[1-deoxy-D-glucitol];

2,2'-[(2,2',4,4',6,6'-hexaiodo-1,1'-biphenyl)-3,3'-diylbis (oxy)]bis[N-(2,3-dihydroxypropyl)acetamide];

2,2'-[(2,2',4,4',6,6'-hexaiodo-1,1'-biphenyl)-3,3'-diylbis (oxy)]bis[N-methylacetamide];

3,3'-[(2,2',4,4',6,6'-hexaiodo-1,1'-biphenyl)-3,3'-diylbis[ (2-hydroxy-1-oxoethyl)imino]bis[1,2-propanediol];

N,N'-[(2,2',4,4',6,6'-hexaiodo-1,1'-biphenyl)-3,3'-diyl]bis [(N,N'-dimethyl)-2-hydroxyacetamide];

2,2'-[(2,2',4,4',6,6'-hexaiodo-1,1'-byphenyl)-3,3'diylbis (oxy)]-bisacetic acid

N,N'-bis[2-hydroxy-1-(hydroxymethyl)ethyl]-5,5'-dihydroxy-2,2',4,4',6,6'-hexaiodo-1,1'-biphenyl-3,3'-dicarboxamide;

N,N'-bis[2-hydroxy-1-(hydroxymethyl)ethyl]-5,5'-bis(3, 6,9,12,15,18,21-heptaoxadocos-1-yloxy)-2,2',4,4',6,6'-hexaiodo-1,1'-biphenyl-3,3'-dicarboxamide;

2,2'-[[5,5'-bis[[[2-hydroxy- 1-(hydroxymethyl)ethyl] amino]carbonyl]-2,2',4,4',6,6'-hexaiodo-1,1'-biphenyl] -3,3'-diylbis(oxy)]bisacetic acid dimethyl ester;

N,N'-bis[2-hydroxy-1-(hydroxymethyl)ethyl]-5,5'-bis[2-[ [2-(hydroxyethoxy)ethyl]methylamino]-2-oxoethoxy]-2,2',4,4',6,6'-hexaiodo-1,1'-biphenyl-3,3'-dicarboxamide.

\* \* \* \* \*